US009980910B2

(12) United States Patent
Cook et al.

(10) Patent No.: US 9,980,910 B2
(45) Date of Patent: May 29, 2018

(54) ENTERIC-COATED SODIUM METABISULFITE LIVESTOCK FEED ADDITIVE FOR VOMITOXIN DETOXIFICATION

(75) Inventors: Douglas R. Cook, Tipp City, OH (US); Keith Adams, Farmersville, OH (US)

(73) Assignee: PROVIMI NORTH AMERICA, INC., Brookville, OH (US)

( * ) Notice: Subject to any disclaimer, the term of this patent is extended or adjusted under 35 U.S.C. 154(b) by 239 days.

(21) Appl. No.: 13/884,859

(22) PCT Filed: Nov. 16, 2011

(86) PCT No.: PCT/US2011/061021
§ 371 (c)(1),
(2), (4) Date: May 10, 2013

(87) PCT Pub. No.: WO2012/068270
PCT Pub. Date: May 24, 2012

(65) Prior Publication Data
US 2013/0230597 A1 Sep. 5, 2013

Related U.S. Application Data

(60) Provisional application No. 61/414,238, filed on Nov. 16, 2010.

(51) Int. Cl.
| | | |
|---|---|---|
| A61K 9/14 | (2006.01) |
| A61K 33/04 | (2006.01) |
| A61K 9/50 | (2006.01) |
| A23K 40/30 | (2016.01) |
| A23K 20/158 | (2016.01) |
| A23K 20/22 | (2016.01) |
| A23K 50/10 | (2016.01) |
| A23K 50/30 | (2016.01) |
| A23K 40/35 | (2016.01) |

(52) U.S. Cl.
CPC ............ A61K 9/145 (2013.01); A23K 20/158 (2016.05); A23K 20/22 (2016.05); A23K 40/30 (2016.05); A23K 50/10 (2016.05); A23K 50/30 (2016.05); A61K 9/5015 (2013.01); A61K 33/04 (2013.01); A23K 40/35 (2016.05)

(58) Field of Classification Search
None
See application file for complete search history.

(56) References Cited

U.S. PATENT DOCUMENTS

| | | |
|---|---|---|
| 2,799,583 A * | 7/1957 | Harris .................. A23K 30/15 426/321 |
| 2,813,299 A | 11/1957 | Massey et al. |
| 2,847,710 A | 8/1958 | Pitzer et al. |
| 3,105,790 A | 10/1963 | Bartholomew |
| 3,249,441 A | 5/1966 | Craig et al. |
| 3,315,589 A | 4/1967 | Hirahara et al. |
| 3,416,928 A | 12/1968 | Freese et al. |
| 3,464,824 A | 9/1969 | Frank et al. |
| 3,573,924 A | 4/1971 | Zarow et al. |
| 3,906,140 A | 9/1975 | Capes et al. |
| 4,153,735 A | 5/1979 | Mommer et al. |
| 4,323,584 A | 4/1982 | Saldien et al. |
| 4,415,547 A | 11/1983 | Yu et al. |
| 4,542,031 A | 9/1985 | Togawa et al. |
| 4,642,238 A | 2/1987 | Lin et al. |
| 4,713,245 A | 12/1987 | Watanabe et al. |
| 4,775,539 A | 10/1988 | Van et al. |
| 4,842,863 A | 6/1989 | Nishimura et al. |
| 4,929,163 A | 5/1990 | Volk |
| 4,988,520 A | 1/1991 | Overton et al. |
| 5,019,148 A | 5/1991 | Moore et al. |
| 5,285,681 A | 2/1994 | Binder et al. |
| 5,391,371 A | 2/1995 | Jensen et al. |
| 5,419,498 A | 5/1995 | Rasmussen et al. |
| 5,556,634 A | 9/1996 | Moore et al. |
| 5,567,452 A | 10/1996 | Rebhan et al. |
| 5,629,038 A | 5/1997 | Kalmbach et al. |
| 5,635,198 A | 6/1997 | Nishimura et al. |
| 5,650,184 A | 7/1997 | Lubbe et al. |

(Continued)

FOREIGN PATENT DOCUMENTS

| | | |
|---|---|---|
| CN | 1069171 | 2/1993 |
| EA | 0040654 A2 | 12/1981 |

(Continued)

OTHER PUBLICATIONS

Awad et al. Decontamination and detoxification strategies for the Fusarium mycotoxin deoxynivalenol in animal feed and the effectiveness of microbial biodegradation. Food Additives and Contaminants, Mar. 2010, vol. 27, Iss 4, pp. 1-28, p. 9, In 260-263, In 279-280.

Danicke, S. et al. "Investigations on the kinetics of the concentration of deoxynivalenol (DON) and on spoilage by moulds and yeasts of wheat grain preserved with sodium metabisulfite (Na2S2O5, SBS) and propionic acid at various moisture contents", Archives of Animal Nutrition, Jun. 2010, 64(3): 199-203, abstract PMID:20578648.

Aliev, A.A. et al. (SU 670293; Translation of Abstract). 1977.

Downloaded from https://en.wikipedia.org/wiki/Molasses on Aug. 13, 2009.

Feeco International, "Complete Systems Solutions Guide" brochure.

Feeco International, "Complete Systems Solutions Guide", brochure.

Feeco International, "Lab Testing + Tolling", brochure.

Feeco International, "Rotary Dryer/Cooler Solutions Guide" brochure.

(Continued)

Primary Examiner — Tigabu Kassa

(57) ABSTRACT

A livestock feed supplement in which a core particle containing sodium metabisulfite and at least one binder is enrobed with an enteric coating, wherein the thickness and composition of the coating protects the sodium metabisulfite from decomposition to sulfur dioxide in an aqueous acid stomach environment. Also disclosed are a method of delivering sodium metabisulfite to the lower gastrointestinal tract of an animal, and a method of delivering an antidote to relieve the toxic effect of vomitoxin in an animal, by administering to the animal the livestock feed supplement.

11 Claims, No Drawings

(56) References Cited

U.S. PATENT DOCUMENTS

| | | | |
|---|---|---|---|
| 5,686,111 A | 11/1997 | Jalbert et al. | |
| 5,686,125 A | 11/1997 | Mueller et al. | |
| 5,786,007 A | 7/1998 | Webb et al. | |
| 5,786,008 A | 7/1998 | Bevans et al. | |
| 5,871,773 A | 2/1999 | Julien et al. | |
| 5,871,802 A | 2/1999 | Crenshaw et al. | |
| 5,935,635 A | 8/1999 | Osada et al. | |
| 6,024,993 A | 2/2000 | Theuninck et al. | |
| 6,120,815 A | 9/2000 | Moore et al. | |
| 6,221,424 B1 | 4/2001 | Kalmbach | |
| 6,238,709 B1 | 5/2001 | Kalmbach | |
| 6,238,727 B1 | 5/2001 | Kato et al. | |
| 6,293,994 B1 | 9/2001 | Field et al. | |
| 6,306,427 B1 | 10/2001 | Laffay et al. | |
| 6,365,208 B1 | 4/2002 | Rogers et al. | |
| 6,436,453 B1 | 8/2002 | Van et al. | |
| 6,500,426 B1 | 12/2002 | Harz et al. | |
| 6,584,700 B1 | 7/2003 | Hawkins | |
| 7,186,533 B2 | 3/2007 | Klein et al. | |
| 7,611,701 B2 | 11/2009 | Harz et al. | |
| 2003/0129295 A1 | 7/2003 | Richardson et al. | |
| 2003/0148013 A1 | 8/2003 | Jobe et al. | |
| 2003/0170371 A1 | 9/2003 | Jobe et al. | |
| 2004/0033985 A1* | 2/2004 | Chi et al. | 514/58 |
| 2004/0052905 A1 | 3/2004 | Pelletier et al. | |
| 2005/0163911 A1 | 7/2005 | McGowen et al. | |
| 2006/0045957 A1 | 3/2006 | Bevans et al. | |
| 2006/0127531 A1 | 6/2006 | Jobe et al. | |
| 2006/0170128 A1 | 8/2006 | Belanger et al. | |
| 2006/0198928 A1 | 9/2006 | Jobe et al. | |
| 2008/0008779 A1 | 1/2008 | Zuccarello et al. | |
| 2008/0031998 A1 | 2/2008 | Marcussen et al. | |
| 2008/0131358 A1 | 6/2008 | Woida et al. | |
| 2009/0317515 A1 | 12/2009 | Lohscheidt et al. | |
| 2010/0022634 A1 | 1/2010 | Holmes et al. | |
| 2010/0055253 A1 | 3/2010 | Gautier et al. | |
| 2010/0092618 A1 | 4/2010 | Jobe et al. | |
| 2010/0226995 A1 | 9/2010 | DeBrouse | |
| 2010/0239537 A1 | 9/2010 | Zhou et al. | |
| 2010/0326151 A1 | 12/2010 | Madigan et al. | |
| 2012/0082721 A1* | 4/2012 | Buessing | A61K 9/5078 424/463 |
| 2013/0064963 A1 | 3/2013 | Leisure et al. | |
| 2013/0089640 A1 | 4/2013 | Lohscheidt et al. | |
| 2013/0136827 A1 | 5/2013 | Drouillard et al. | |
| 2013/0305793 A1 | 11/2013 | Moore et al. | |

FOREIGN PATENT DOCUMENTS

| | | |
|---|---|---|
| EP | 0090995 A1 | 10/1983 |
| EP | 0125894 A2 | 11/1984 |
| EP | 749698 A2 | 12/1996 |
| EP | 2413339 A1 | 2/2012 |
| FR | 2796522 A1 | 1/2001 |
| GB | 1316377 A | 5/1973 |
| GB | 2123671 A | 2/1984 |
| RU | 2354403 C2 | 5/2009 |
| WO | 9809538 | 3/1998 |
| WO | 0101790 A1 | 1/2001 |
| WO | 2006034098 A1 | 3/2006 |
| WO | 2007054465 A1 | 5/2007 |
| WO | 2011041083 A1 | 4/2011 |
| WO | 2011091111 A1 | 7/2011 |
| WO | 2012134942 A1 | 10/2012 |
| WO | 2015050955 A1 | 4/2015 |

OTHER PUBLICATIONS

International Search Report dated Dec. 30, 2014 for International Application No. PCT/US2014/058574 (3 pages).

International Search Report PCT/US2005/033287, Jan. 19, 2008.

Super-Lube Feed Additives, Lubricant for Hard-To-Pellet-Feeds, Uniscope, Inc.. 2007.

"Disc Pelletizer", Feeco International "Disc Pelletizer" brochure.

"Feeds and Feeding", Cullison, A.E., Feeds and Feeding, No. Ed. 3, 1982, pp. 75-76; ISBN: 0835919056; Reston Publishing Co., Inc.

"Granulor", Vitamex, 2003.

"*Hansgirg* v. *Kemmer*", Court of Customs and Patent Appeals, Appl. No. 4077, 40 USPQ 665, Feb. 27, 1939, 1-4.

"Sheep Feed Composition", Derwent Record, Aliev, A.A., SU0670293T.

"*Verdegeal Brothers Inc.* v. *Union Oil Company of California*", U.S. Court of Appeals Federal Circuit, 2 USPQ2d 1051, No. 86-1258, 814 F2d 628, Mar. 12, 1987, 1-5.

Albert, et al., "Pelletizing Limestone Fines—A Study of the Benefits of Pelletized Limestone Fines in the Commercial and Agricultural Market", Albert, Kurt B., and Don Langford. "Pelletizing Limestone Fines." Mars Mineral, Pennsylvania (1998): 12-29.

Gantner, "Capturing lost profits with agglomeration", Powder and Bulk Engineering, vol. 21, No. 2, Feb. 2007, 23-28.

McDonald, et al., "Recent developments in soluble silicate-based binders", Powder and Bulk Engineering, Feb. 2009, 30-35.

Mommer, et al., "A Guide to Feed Pelletizing Technology", Uniscope, Inc., 2002, 1-22.

Pietsch, "An introduction to growth-tumble and pressure agglomeration", Powder and Bulk Engineering, vol. 20, No. 2, Feb. 2006, 27-32.

Pittenger, et al., "How to minimize feed segregation to an agglomerator—Part I", Powder and Bulk Engineering, vol. 22, No. 2, Feb. 2008, 21-26.

Stewart, et al., "Mineral Supplements for Beef Production", The University of Georgia College of Agriculture & Environmental Sciences Cooperative Extension Service, 1994, 1-9.

Veverka, et al., "A Comparison of Liquid Binders for Limestone Pelletizing", Veverka, Jim, and Robert Hinide. "A comparison of liquid binders for limestone pelletizing." Biennial Conference-Institute of Briquetting and Agglomeration. vol. 27. Institute for Briquetting and Agglomeration, 2001.

* cited by examiner

ENTERIC-COATED SODIUM METABISULFITE LIVESTOCK FEED ADDITIVE FOR VOMITOXIN DETOXIFICATION

CROSS-REFERENCE TO RELATED APPLICATION

This application is a national phase application of international application PCT/US11/061021, filed Nov. 16, 2011, which application claims priority to U.S. Application, Ser. No. 61/414,238, filed Nov. 16, 2010, which applications are hereby incorporated by reference herein in their entirety.

BACKGROUND OF THE INVENTION

Vomitoxin (deoxynivalenol or DON) is a trichothecene mycotoxin produced by *Fusarium* molds which occurs on cereal grains intended for consumption by livestock. Vomitoxin contamination of grains is documented to have toxic effects in many species, including pigs which appear to be the most sensitive of any species tested. Vomitoxin levels as low as 0.6 to 2.0 ppm in complete feed cause a reduction in feed intake and growth rate. Higher levels, above 5 ppm, can result in complete feed refusal, vomiting, immune suppression, and gastrointestinal lesions.

Sodium metabisulfite ($NaS_2O_5$) and sodium bisulfite ($Na_2SO_3$) have been shown to destroy vomitoxin in processed grains. The extent of destruction is dependent on heat, moisture level, and time. Feeding sodium metabisulfite to pigs has been tested in a toxicology study (The Toxicity of Sulphite. II. Short and Long-Term Feeding Studies in Pigs. H. P. Til, V. J. Feron, A. P. De Groot and P. Van Der Wal. *Fd Cosmet. Toxicol.* Vol. 10, pp. 463-473. Pergamon Press 1972. Printed in Great Britain.) and can be achieved with no toxic effects at levels up to 0.35% of the diet, the "no-effect" level established in the study. In view of the toxicity of vomitoxin and the toxicity of sodium metabisulfite above 0.35 wt % in pig diets, the need exists for a livestock supplement having a non-toxic level of sodium metabisulfite that is effective to reduce the toxic effects of vomitoxin.

SUMMARY OF THE INVENTION

The present invention incorporates the discovery that the small intestine or equivalent higher pH portions of the gastrointestinal tract provides a more ideal environment than the monogastric stomach or similar environments to destroy vomitoxin with sodium meta-bisulfite. While not being bound by any particular theory, it is believed that the agent binds to and prevents adsorption of the toxin. Accordingly, the present invention provides a product and method for delivering sodium metabisulfite to the lower gastrointestinal tract as an antidote for the ingestion of vomitoxin by a mammal.

Therefore, according to one aspect of the present invention, a livestock feed supplement is provided in which a core particle containing sodium metabisulfite and at least one binder is enrobed with an enteric coating, wherein the thickness and composition of the coating protects the sodium metabisulfite from decomposition to sulfur dioxide in an aqueous acid stomach environment. According to one embodiment, the binder is a pellet binder, a starch binder or a fiber binder.

According to an embodiment, the binder is a water-soluble binder selected from starch, sodium caseinate, gelatin, soybean protein, molasses, lactose, dextrin, carboxymethyl cellulose salt, alginates, methyl cellulose, ethyl cellulose, hydroxypropyl cellulose, starch glycolic acid salt, polymethacrylates, polyvinyl alcohol and polyvinyl pyrrolidone. According to another embodiment, the binder is a hydrophobic binder selected from natural waxes, shellac resin, rosin, bees wax, paraffin wax cetanol, higher fatty acids, stearic acid, stearic acid metal salts, animal fats, animal oils, vegetable fats, vegetable oils, palm oil, hardened animal fats, hardened animal oils, hardened vegetable fats, hardened vegetable oils; nonionic surfactants, glycerin monostearate; semi-synthetic resins, synthetic high-molecular substances, acetyl cellulose, polyvinyl acetate, ester gum and coumarone resin.

In one embodiment, the enteric coating is a highly hydrogenated vegetable oil selected from cottonseed, corn, peanut, soybean, palm, palm kernel, babassu, sunflower, safflower, and combinations or two or more thereof. In another embodiment, the highly hydrogenated vegetable oil is soybean oil.

In yet another embodiment, the enteric coating further includes:
  (a) one or more wax components selected from paraffin wax, petroleum wax, cetanol, mineral wax, ozokerite, ceresin, utah wax, montan wax, vegetable wax, rice bran wax, castor wax, carnuba wax, Japan wax, bayberry wax, flax wax, rosin, insect wax, beeswax, Chinese wax, shellac wax, and gums; and/or
  (b) one or more glycerides selected from mono-glycerides, di-glycerides, and mixtures thereof, extracted from vegetable oils selected from cottonseed, corn, peanut, soybean, palm, palm kernel, babassu, sunflower, safflower, and combinations of two or more thereof; and/or
  (c) one or more additional ingredients selected from mineral oil, glycerin, lecithin, gums and alginates.

In one embodiment, the one or more wax components include beeswax. In another embodiment, the one or more glycerides have between 10 and 22 carbon atoms.

According to another aspect of the present invention, a method for delivering sodium metabisulfite to the lower gastrointestinal tract of an animal is provided by administering to the animal the livestock feed supplement of the present invention. The method can be used as a means for delivering an antidote to relieve the toxic effects of vomitoxin in a mammal. The toxic effects include at least one selected from reduction in feed intake, reduction in growth rate, feed refusal, vomiting, immune suppression and gastrointestinal lesions. In one embodiment the animal is selected from dairy and beef cattle, broiler and laying hen chickens, ducks, goats, pigs, sheep and turkeys.

A more complete appreciation of the invention and many other intended advantages can be readily obtained by reference to the following detailed description of the preferred embodiments and claims, which disclose the principles of the invention and the best modes which are presently contemplated for carrying them out.

DETAILED DESCRIPTION OF THE INVENTION

The present invention relates to a livestock feed supplement for reducing the toxic effects of vomitoxin in livestock. As used herein, the term "livestock" includes, but is not limited to, dairy and beef cattle, broiler and laying hen chickens, ducks, goats, pigs, sheep, and turkeys. The supplement includes a core particle that includes sodium metabisulfite and at least one binder; and an enteric coating enrobing the core particle.

The binder(s) may include any pellet binder, starch binder, fiber binder, or any similar binder otherwise known in the art. For example, the binder may be any water-soluble type binder including, but not limited to, starch, sodium caseinate, gelatin, soybean protein, molasses, lactose, dextrin, carboxymethyl cellulose salt, alginates, methyl cellulose, ethyl cellulose, hydroxypropyl cellulose, starch glycolic acid salt, and synthetic high-molecular substances such as polymethacrylates, polyvinyl alcohol and polyvinyl pyrrolidone.

Alternatively, the binder may be comprised of any hydrophobic type binder including, but not limited to, natural waxes such as shellac resin, rosin, bees wax and paraffin wax; cetanol, higher fatty acids such as stearic acid and metal salts thereof; materials associated with fats and oils, such as animal and vegetable fats and oils, for example, palm oil and hardened animal and vegetable fats and oils; nonionic surfactants such as glycerin mono-stearate; and semi-synthetic resins and synthetic high-molecular substances such as acetyl cellulose, polyvinyl acetate, ester gum and coumarone resin. To this end, the composition of the binder is not necessarily limiting to the present invention and any binder known in the art may be used.

Sodium metabisulfite will decompose quickly under aqueous acid conditions (e.g. monogastric stomach) to form sodium bisulfite and sulfur dioxide. Sodium bisulfite will subsequently decompose into sodium oxide and sulfur dioxide. When fed to an animal, little if any metabisulfite will remain intact when the stomach empties into the small intestine, and the sulfur dioxide produces deleterious effects. Thus, any action of sodium metabisulfite on vomitoxin when fed to a mammal is in the stomach.

To deliver intact sodium metabisulfite to an area of the lower gastrointestinal tract such as the small intestine, an enteric coating is used. The coating protects sodium metabisulfite from exposure to an aqueous acid environment and thus decomposition in the stomach or similar environments where sodium metabisulfite is decomposed to sulfur dioxide. The coating is removed, fractured, or degraded by the action of intestinal lipase, increased pH level vs. the stomach, bile salts, or time exposed to an aqueous environment. This allows intact sodium metabisulfite to act on vomitoxin at a pH level where sodium metabisulfite can be most effective at destroying vomitoxin and will thus lower the amount of sodium metabisulfite required to elicit a positive effect in the presence of vomitoxin. It also improves the response to sodium metabisulfite in the presence of vomitoxin and will thus restore a higher percentage of lost growth performance from vomitoxin consumption.

One such method of creating a protective coating consists of creating a core particle consisting of sodium metabisulfite and a binder, such as a pellet binder, starch binder, fiber binder, or any water soluble type binder or hydrophobic type binder. In one embodiment, the binder may be composed of lignin sulfonate. The resulting core particle is subsequently enrobed utilizing an elastic coating composition which may be formed from fats, fatty acids, highly hydrogenated oils, waxes, glycerides, or other materials which are resistant to an acid pH and thus will remain intact or un-degraded in the stomach thus protecting the core particle from exposure and subsequent decomposition in the stomach. The coating may provide 20-70% w/v of the final product.

In one embodiment, the base component of the coating composition is a highly hydrogenated oil. As used herein, the phrase "highly hydrogenated" or "highly saturated" refers to oils having carbon chains entirely or almost entirely saturated with hydrogen atoms (i.e. relatively few carbon-to-carbon double bonds). In one embodiment, the highly hydrogenated oils refer to vegetable oil extracts including, but not limited to, those of cottonseed, corn, peanut, soybean, palm, palm kernel, babassu, sunflower, safflower, and combinations thereof. In certain non-limiting embodiments, the highly hydrogenated vegetable oil is extracted from soybean.

In further embodiments, the coating composition includes a wax component. The wax component may be comprised of any wax that is known in the art. Non-limiting examples of such waxes may include, but are not limited to, paraffin wax, petroleum wax, cetanol, mineral wax (e.g. ozokerite, ceresin, utah wax, montan wax, etc.), a vegetable wax (e.g. rice bran wax, castor wax, carnuba wax, Japan wax, bayberry wax, flax wax, rosin, etc.), an insect wax (e.g. beeswax, Chinese wax, shellac wax, etc.), or gums which are otherwise known in the art. In certain embodiments, the wax is comprised of beeswax.

The wax component of the coating may be provided in any amount to contribute to the hydrophobic aspect of the coating composition. In one embodiment, the wax may comprise between about 0.1% to 25% of the coating composition. In a further embodiment, the wax component may comprise between 2.0% and 15.0% of the coating composition. In a further embodiment, the wax component may comprise between 2.5% and 10.0% of the coating composition. In certain embodiments, the wax component comprises 2.5%, 5.0%, 7.5%, 8.25% or 10% of the coating composition. The wax component of the coating, however, is not limited to this range and may be provided in any amount to achieve the objectives and advantages discussed herein.

In even further embodiments the coating composition contains a glyceride component. While not limited thereto, the glyceride component may be comprised of mono-glycerides, di-glycerides, or combinations thereof. To this end, the glyceride component of the present invention may be comprised of a mixture of mono- and di-glycerides. In such embodiments, the mono-glycerides may comprise 40-75% of the glyceride component and di-glycerides may comprise 25-60% of the glyceride component. In further embodiments, about 52% of the glyceride component is comprised of mono-glycerides and about 48% is comprised of di-glycerides.

Mono-glycerides, di-glycerides, and mixtures thereof may be obtained from any source with chain lengths of any length known in the art. In one embodiment, they may be a mixture extracted from vegetable oil such as, but not limited to, cottonseed, corn, peanut, soybean, palm, palm kernel, babassu, sunflower, safflower, and combinations thereof. While they may be of any length, the mono- and di-glycerides, in certain embodiments, have between 10 and 22 carbon atoms.

The glyceride component of the coating may be provided in any amount to contribute to objectives and advantages discussed herein. In one embodiment, the glyceride component may comprise between about 0.01% to 10.0% of the coating composition, with less than 1.5% of the glyceride component being comprised of free glycerin. In further embodiments, the glyceride component may comprise between 1.0% and 5.0% of the coating composition, with less than 1.5% of the glyceride component being comprised of free glycerin. In certain embodiments the glyceride components comprise about 0.72%, 1.3%, 1.8%, 2.0%, 2.5%, or 3.6% of the coating composition, again, with less than 1.5% of the glyceride component being comprised of free glycerin. The glyceride component of the coating, however, is not limited to these ranges and may be provided in any amount to contribute to objectives and advantages discussed herein.

The coating may also be comprised of one or more additional ingredients such as binders, fillers, lubricants, or the like. Such additional ingredients may include but are not limited to one or a combination of Mineral Oil, Glycerin Lecithin, Gums, or Alginates.

Enrobing the particle cores with the foregoing coating composition may be performed by any method known in the art, particularly those achieving uniformity in coating. In one embodiment, for example, the core particles are coated using a Falling Curtain drum process and a high pressure pump. Specifically, the particle cores are first preheated to approximately 140 to 150° F., then the coating is applied with a high pressure pump and spray nozzle. In certain embodiments, the coating is applied at 205 to 210° F., at a coating spray pressure of about 300 to 350 PSIG. In even further embodiments, the coating bed temperature is approximately 110 to 120° F. and the drum speed is approximately 16 rpm.

The coating step, however, is not confined to using a Falling Curtain drum. Rather, other coating techniques known in the art may be used such as, but not limited to, fluidized bed coating, pan dish coating. Alternative methods may include, but are not limited to, those methods disclosed in U.S. Pat. Nos. 4,511,584; 4,537,784; 4,497,845; 3,819,838; 3,341,446; 3,279,994; 3,159,874; 3,110,626; 3,015,128; 2,799,241; and 2,648,609, all of which are incorporated herein by reference.

The following non-limiting examples set forth herein below illustrate certain aspects of the invention.

EXAMPLES

Example 1

Effects of Sodium Metabisulfite in Contaminated Diets

The toxic effect of vomitoxin in feed for pigs is evidenced by the results shown below in Table 1. A diet containing approximately 5 ppm vomitoxin reduced daily feed intake and growth rate in 25-55 lb pigs by 20 and 15 percent, respectively (P<0.01).

TABLE 1

Impact of feeding vomitoxin-contaminated corn with increasing levels of sodium metabisulfite on growth performance of 25-50 lb pigs (F3_N07_05).

| | Corn Source: | | | | |
| --- | --- | --- | --- | --- | --- |
| | Control | Contaminated | | | |
| Defusion: | 0 lbs | 0 lbs | 5 lbs | 10 lbs | 20 lbs |
| Initial Wt (lb) | 24.3 | 25.1 | 24.6 | 24.7 | 24.8 |
| Final Wt (lb) (ab) | 55.0 | 51.0 | 53.2 | 53.7 | 52.2 |
| ADG (lb) (ab) | 1.32 | 1.12 | 1.23 | 1.25 | 1.21 |
| ADFI (lb) (ab) | 2.08 | 1.67 | 1.83 | 1.85 | 1.84 |
| FG (lb/lb) (a) | 1.57 | 1.50 | 1.48 | 1.48 | 1.52 |

TABLE 1-continued

Impact of feeding vomitoxin-contaminated corn with increasing levels of sodium metabisulfite on growth performance of 25-50 lb pigs (F3_N07_05).

| | Corn Source: | | | | |
| --- | --- | --- | --- | --- | --- |
| | Control | Contaminated | | | |
| Defusion: | 0 lbs | 0 lbs | 5 lbs | 10 lbs | 20 lbs |
| Mortality & Removals, % | 2.3 | 5.4 | 2.2 | 4.1 | 2.3 |
| Vomitoxin, ppm | 1.8 | 8.8 | 5.6 | 5.0 | 3.7 |

(a) Clean vs. Contaminated, P < .01
(b) Defusion effect quadratic, P < .01.

Example 2

Effects of Sodium Metabisulfite in Clean Diets

The data presented in Table 2 confirms that toxic effects begin to occur between 0 and 0.5% sodium metabisulfite in the diet. Average daily feed intake was linearly reduced as sodium metabisulfite level increased from 0 to 0.5 to 1.0% in non-vomitoxin contaminated diets.

TABLE 2

Effect of feeding sodium metabisulfite in clean diets on growth performance of 66-278 lbs pigs (F6_G07_01).

| | Defusion Level, lbs/ton | | |
| --- | --- | --- | --- |
| | 0 | 10 | 20 |
| Initial wt., lb | 66.3 | 66.7 | 66.6 |
| Final wt., lb | 279.2 | 278.7 | 273.5 |
| ADG, lb (a) | 1.94 | 1.94 | 1.89 |
| ADFI, lb (b) | 5.52 | 5.46 | 5.26 |
| F/G | 2.84 | 2.81 | 2.80 |

(a) Defusion effect linear P < .10.
(b) Defusion effect linear P < .05.

Example 3

Effects of Additives in High Vomitoxin Diets

Feeding sodium metabisulfite to pigs consuming a diet contaminated with vomitoxin improves (P<0.01) average daily gain (ADG) and average daily feed intake (ADFI) at levels of sodium metabisulfite ranging from 5 to 20 lbs/ton of diet, or 0.25 to 1.0% (Table 1). This was confirmed in a second trial shown in Table 3, using a product ("Defusion") comprising primarily (greater than 97%) sodium metabisulfite, at levels ranging from 0.125 to 0.5% of the diet. In this second trial, the response to Defusion improved with increasing levels of Defusion (P<0.01).

TABLE 3

Effects of additives on performance of nursery pigs fed high vomitoxin (F3-N09-46_47).

| Phase 4 (21-22 days) | PC | NC | NC + Defusion, % | | | NC + Defusion Plus, % | | 0.10% Biofix | 0.20% Unike |
|---|---|---|---|---|---|---|---|---|---|
| | | | 0.125 | 0.25 | 0.5 | 0.125 | 0.25 | | |
| Initial wt, kg | 11.63 | 11.60 | 11.40 | 11.53 | 11.33 | 11.57 | 11.43 | 11.76 | 11.40 |
| Final wt, kg (ac) | 22.55 | 20.97 | 21.60 | 21.56 | 21.82 | 21.40 | 21.21 | 20.83 | 20.70 |
| ADG, kg/d (abg) | 0.508 | 0.436 | 0.474 | 0.467 | 0.487 | 0.457 | 0.455 | 0.421 | 0.433 |
| ADFI, kg/d (ab) | 0.830 | 0.700 | 0.732 | 0.736 | 0.764 | 0.712 | 0.705 | 0.697 | 0.701 |
| Gain to feed, kg/kg | 0.613 | 0.623 | 0.649 | 0.635 | 0.638 | 0.642 | 0.646 | 0.605 | 0.617 |
| Cost per kg gain, USD/kg (fg) | 0.492 | 0.484 | 0.469 | 0.482 | 0.487 | 0.475 | 0.478 | 0.508 | 0.502 |
| Mortality & removals, % | 1.8 | 4.6 | 4.2 | 5.3 | 2.3 | 6.5 | 8.2 | 4.0 | 1.7 |
| Mortality, % | 1.2 | 1.7 | 1.2 | 3.0 | 0.6 | 0.6 | 1.2 | 0.6 | 0.6 |
| Removals, % (de) | 0.6 | 2.9 | 3.0 | 2.3 | 1.7 | 5.9 | 7.0 | 3.5 | 1.1 |

(a) PC vs. NC (P < 0.01)
(b) Defusion Linear (P < 0.01)
(c) Defusion Linear (P < 0.10)
(d) Defusion Plus Linear (P < 0.05)
(e) NC vs. Defusion Plus (P < 0.05)
(f) NC vs. Biofix (P < 0.05)
(g) NC vs. Nutrisound (P < 0.10)

Example 4

Destruction of Vomitoxin by Sodium Metabisulfite In Vitro

Sodium metabisulfite was tested for its ability to destroy vomitoxin in vitro at different pH levels. Data in Table 4 demonstrates that sodium metabisulfite destroys more vomitoxin at a neutral pH (pH 6.5) vs. an acidic pH (pH 3.0). For example, when tested at 10 lb/ton, sodium metabisulfite destroyed 70% of the measurable vomitoxin at pH 6.5, but none at pH 3.0. At 20 lbs/ton sodium metabisulfite destroyed over 97% of the vomitoxin at pH 6.5 but only 41% at pH 3.0. Destruction levels less than 10% are considered to be random variation in this assay and not related to treatment. Thus sodium metabisulfite is more effective at detoxifying vomitoxin at a pH similar to that of an animal's small intestine vs. that of its stomach. Although the levels of sodium metabisulfite required to destroy vomitoxin in this in vitro assay are higher than the "safe" level of 0.35% determined in a previous referenced feeding trial in pigs, other studies (Tables 1 and 3) clearly show positive effects of sodium metabisulfite at levels of 0.125 to 0.25% in vomitoxin-contaminated diets. Thus in vitro levels of sodium metabisulfite required to product effects in vitro do not correlate perfectly with levels required to product positive effects in vivo. In vitro results show close to 100% destruction of vomitoxin occurs at higher pH levels (e.g. 6.5) vs. only 41% at acidic pH levels. The in vivo feeding trials (Tables 1 and 3) show that significantly less than 100% of the feed intake and growth rate reduction caused by vomitoxin can be recovered by feeding sodium metabisulfite to pigs.

TABLE 4

Percent destruction of vomitoxin by sodium metabisulfite in vitro at two pH levels.

| | % Destruction | | | |
|---|---|---|---|---|
| Metabisulfite, lbs/ton: | 2.5 | 5 | 10 | 20 |
| % destruction at pH 3.0 | 4.2 | 0.9 | 0.0 | 41.0 |
| % destruction at pH 6.5 | 0.0 | 0.0 | 70.0 | 97.7 |

Example 5

Coating Batches

The following batches are prepared for analysis:

| | Coating Composition % | | | | | |
|---|---|---|---|---|---|---|
| Batch | Soybean Oil | Bees Wax | Mono-Glyceride | Di-Glyceride | Part. Hydrog Soy Oil | Other* |
| A | 30 | 7.5 | 1.8 | | | |
| B | 30 | 5.0 | 3.6 | | | |
| C | 30 | 5.0 | 7.2 | | | |
| D | 30 | 7.5 | 0.25 | 1.83 | | |
| E | 30 | 7.5 | 1.05 | | | |
| F | 30 | 7.5 | 1.3 | | | |
| G | 30 | 7.5 | | | 2.5 | |
| H | 32.5 | 10 | 1.8 | | | |
| I | 30 | 10 | | | | |
| J | 31.75 | 8.25 | | | | |
| K | 40 | 10 | | | | |
| L | 30 | 15 | | | | |
| M | 30 | 10 | 1.8 | | | |
| N | 30 | 10 | 0.25 | 1.83 | | |
| O | 30 | 10 | 0.25 | 1.83 | | |
| P | 30 | 10 | | | | 5.0 |
| Q | 30 | 10 | | | | 2.5 |
| R | 30 | 10 | | | | 1.0 |
| S | 30 | 10 | | | | 1.0 |
| T | 30 | 10 | | | | 0.1 |
| U | 30 | 10 | | | 1.0 | |
| V | 30 | 10 | | | 1.0 | |

-continued

Coating Composition %

| Batch | Soybean Oil | Bees Wax | Mono-Glyceride | Di-Glyceride | Part. Hydrog Soy Oil | Other* |
|---|---|---|---|---|---|---|
| W | 30 | 10 | | | | 1.0 |
| X | 3430 | 5 | 0.72 | | | |
| Y | 35 | 2.5 | 1.8 | | | |
| Z | 25 | 2.5 | 1.8 | | | |
| AA | 37.5 | | 1.8 | | | |
| BB | 30 | | 1.8 | | | |
| CC | 25 | 2.5 | 1.8 | | | |
| DD | 25 | 2.5 | 1.8 | | | |
| EE | 30 | 10 | | | | |
| FF | 30 | 10 | | | | |
| GG | 30 | 7.5 | 1.3 | | | |
| HH | 30 | 7.5 | 1.3 | | | |
| II | 30 | 7.5 | 1.3 | | | |
| JJ | 30 | 7.5 | 1.3 | | | |
| KK | 30 | 7.5 | 1.3 | | | |
| LL | 30 | 7.5 | 1.3 | | | |
| MM | 30 | 7.5 | 1.3 | | | |

Other includes one or a combination of Mineral Oil, Glycerin Lecithin, Gums, Alginates The foregoing examples illustrate how the present invention allows sodium metabisulfite to pass through the stomach (acidic pH) unaltered and be released in the small intestine (higher pH) where it is most effective at destroying vomitoxin. These examples, and the foregoing description of the preferred embodiment, should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A livestock feed diet comprising a livestock feed supplement comprising:

(a) a core particle consisting of sodium metabisulfite and at least one binder, and (b) an enteric coating enrobing said core particle, wherein the coating is 20-70% w/v of the livestock feed diet and the thickness of said coating protects said sodium metabisulfite from decomposition to sulfur dioxide in an aqueous acid stomach environment, wherein the level of sodium metabisulfite is in the range of 0.125 to 1.0 weight % of the livestock feed diet.

2. The livestock feed diet of claim 1, where the level of sodium metabisulfite is in the range of 0.125 to 0.5 weight % of the livestock feed diet.

3. The livestock feed diet of claim 1, where the level of sodium metabisulfite is in the range of 0.125 to 0.25 weight % of the livestock feed diet.

4. The livestock feed diet of claim 1, wherein said binder is selected from the group consisting of a pellet binder, a starch binder, and a fiber binder.

5. The livestock feed diet of claim 1, wherein said binder is a water-soluble binder selected from the group consisting of starch, sodium caseinate, gelatin, soybean protein, molasses, lactose, dextrin, carboxymethylcellulose salt, alginates, methyl cellulose, ethyl cellulose, hydroxypropyl cellulose, starch glycolic acid salt, polymethacrylates, polyvinyl alcohol and polyvinyl pyrrolidone.

6. The livestock feed diet of claim 1, wherein said binder is a hydrophobic binder selected from the group consisting of natural waxes, shellac resin, rosin, bees wax, paraffin wax, cetanol, higher fatty acids, stearic acid, stearic acid metal salts, animal fats, animal oils, vegetable fats, vegetable oils, palm oil, hardened animal fats, hardened animal oils, hardened vegetable: tats, hardened vegetable oils, nonionic surfactants, glycerin monostearate, semi-synthetic resins, synthetic high-molecular weight substances, acetyl cellulose, polyvinyl acetate, ester gum and coumarone resin.

7. The livestock feed diet of claim 1, wherein said enteric coating comprises a highly hydrogenated vegetable oil selected from the group consisting of cottonseed, corn, peanut, soybean, palm, palm kernel, babassu, sunflower, safflower and combinations or two or more thereof.

8. The livestock feed diet of claim 7, wherein said highly hydrogenated vegetable oil comprises soybean oil.

9. The livestock feed diet of claim 7, wherein said enteric coating further comprises:

(a) one or more wax components selected from the group consisting of paraffin wax, petroleum wax, cetanol, mineral wax, ozokerite, ceresin, utah wax, montan wax, vegetable wax, rice bran wax, castor wax, carnuba wax, Japan wax, bayberry wax, flax wax, rosin, insect wax, beeswax, Chinese wax, shellac wax and gums; and/or (b) one or more glycerides selected from the group consisting of monoglycerides, di-glycerides and mixtures thereof, extracted from vegetable oils selected from the group consisting of cottonseed, corn, peanut, soybean, palm, palm kernel, babassu, sunflower, safflower and combinations of two or more thereof; and/or (c) one or more additional ingredients selected from the group consisting of mineral oil, glycerin, lecithin, gums and alginates.

10. The livestock feed diet of claim 9, wherein said one or more wax components comprises beeswax.

11. The livestock feed diet of claim 9, wherein said one or more glycerides have between 10 and 22 carbon atoms.

* * * * *

UNITED STATES PATENT AND TRADEMARK OFFICE
CERTIFICATE OF CORRECTION

PATENT NO. : 9,980,910 B2
APPLICATION NO. : 13/884859
DATED : May 29, 2018
INVENTOR(S) : Douglas E. Cook et al.

It is certified that error appears in the above-identified patent and that said Letters Patent is hereby corrected as shown below:

On the Title Page

In Column 2, under "FOREIGN PATENT DOCUMENTS", Line 2, delete "EA" and insert -- EP --, therefor.

In the Claims

In Column 10, Line 28, in Claim 7, after "combinations" delete "or" and insert -- of --, therefor.

Signed and Sealed this
Second Day of October, 2018

Andrei Iancu
*Director of the United States Patent and Trademark Office*